US00PP35358P2

(12) United States Plant Patent
Asanoma

(10) Patent No.: US PP35,358 P2
(45) Date of Patent: Aug. 29, 2023

(54) ***AJUGA* PLANT NAMED 'ASAAJ1'**

(50) Latin Name: *Ajuga reptans*
Varietal Denomination: ASAAJ1

(71) Applicant: Asanoma Engei, Kitashitara-gun (JP)

(72) Inventor: Tatsuya Asanoma, Aichi-prefecture (JP)

(73) Assignee: Asanoma Engei

( * ) Notice: Subject to any disclaimer, the term of this patent is extended or adjusted under 35 U.S.C. 154(b) by 0 days.

(21) Appl. No.: 18/085,436

(22) Filed: Dec. 20, 2022

(51) Int. Cl.
*A01H 6/00* (2018.01)
*A01H 5/02* (2018.01)

(52) U.S. Cl.
USPC ..... Plt./401

(58) Field of Classification Search
USPC ..... Plt./401
CPC ..... A01H 6/00; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Ajuga reptans* plant named 'ASAAJ1' is disclosed, characterized by green foliage with a silvery-blue layer. Plants are low growing and compact, having a groundcover habit. Low maintenance plants with violet-blue flowers. The new variety is an *Ajuga*, useful for a variety of ornamental purposes, including outdoor containers and landscape.

3 Drawing Sheets

Latin name of the genus and species: *Ajuga reptans.*
Variety denomination: 'ASAAJ1'.

BACKGROUND OF THE INVENTION

The new *Ajuga* cultivar is the product of chance discovery. The new variety was discovered as a naturally occurring whole plant mutation of the parent variety, *Ajuga reptans* 'White Variegata', unpatented.

The discovery was made in the inventor's garden in Aichi-prefecture, Japan, during the Spring of 2015.

Asexual reproduction of the new cultivar 'ASAAJ1' was first performed in Aichi-prefecture, Japan by terminal vegetative cuttings in February of 2016. 'ASAAJ1' has since produced multiple generations and has shown that the unique features of this cultivar are stable and reproduced true to type.

SUMMARY OF THE INVENTION

The cultivar 'ASAAJ1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ASAAJ1' These characteristics in combination distinguish 'ASAAJ1' as a new and distinct *Ajuga reptans* cultivar:

1. Green leaves with a silvery-blue layer.
2. Compact, groundcover habit.
3. Blue-purple flowers.
4. Low maintenance plant.

PARENTAL COMPARISON

Plants of the new cultivar 'ASAAJ1' are similar to plants of the parent in most horticultural characteristics, however, plants of the new cultivar 'ASAAJ1' differ in the following:

1. Foliage of the new variety is green with a silvery-blue layer, while foliage of the parent variety is white with green margins.
2. The new variety has larger leaves than the parent.
3. The new variety is easier and faster to propagate than the parent.

COMMERCIAL COMPARISON

Plants of the new cultivar 'ASAAJ1' are comparable to the known, unpatented, *Ajuga* 'ASAAJ3', U.S. Plant Pat. No. 33,082. Plants are similar in most horticultural characteristics; however, the new variety 'ASAAJ1' differs in the following:

1. Foliage of the new variety is green with a silvery-blue layer, while foliage of this comparator is variegated creamy-white with dark green.

BRIEF DESCRIPTION OF THE PHOTOGRAPHS

The accompanying photograph in FIG. 1 illustrates in full color a typical plant of 'ASAAJ1' grown outdoors in Boskoop, NL. Age of the plant is approximately 18 months.

Figure 1:
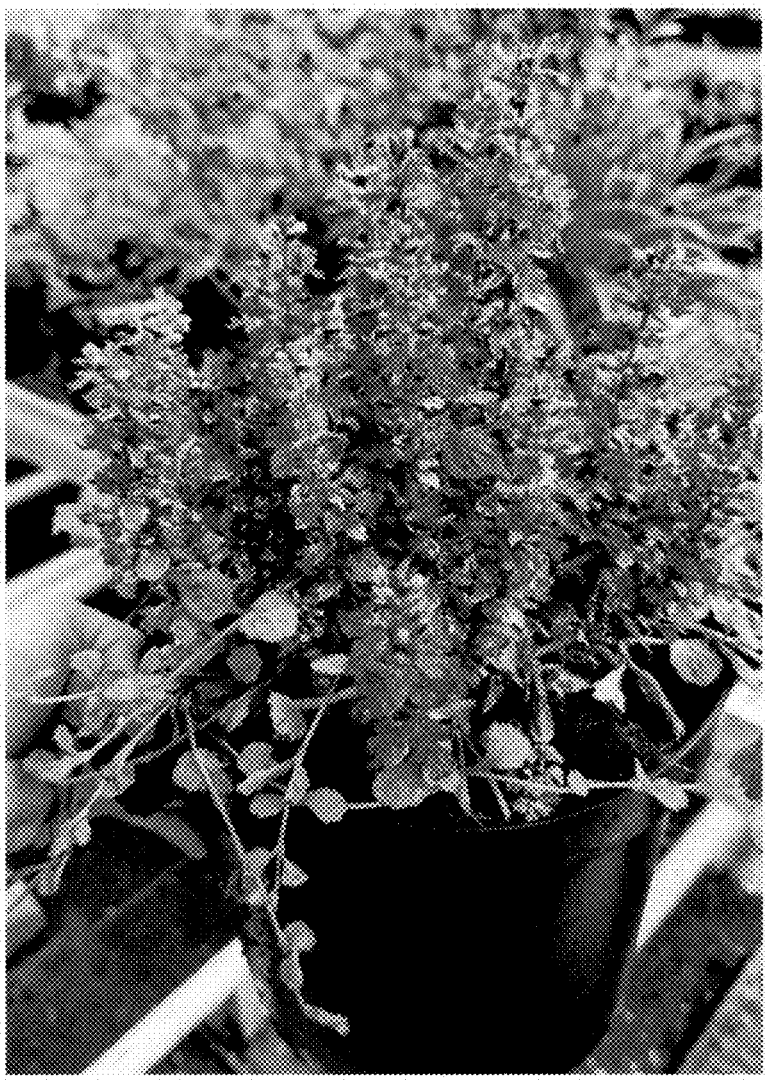
Figure 2:
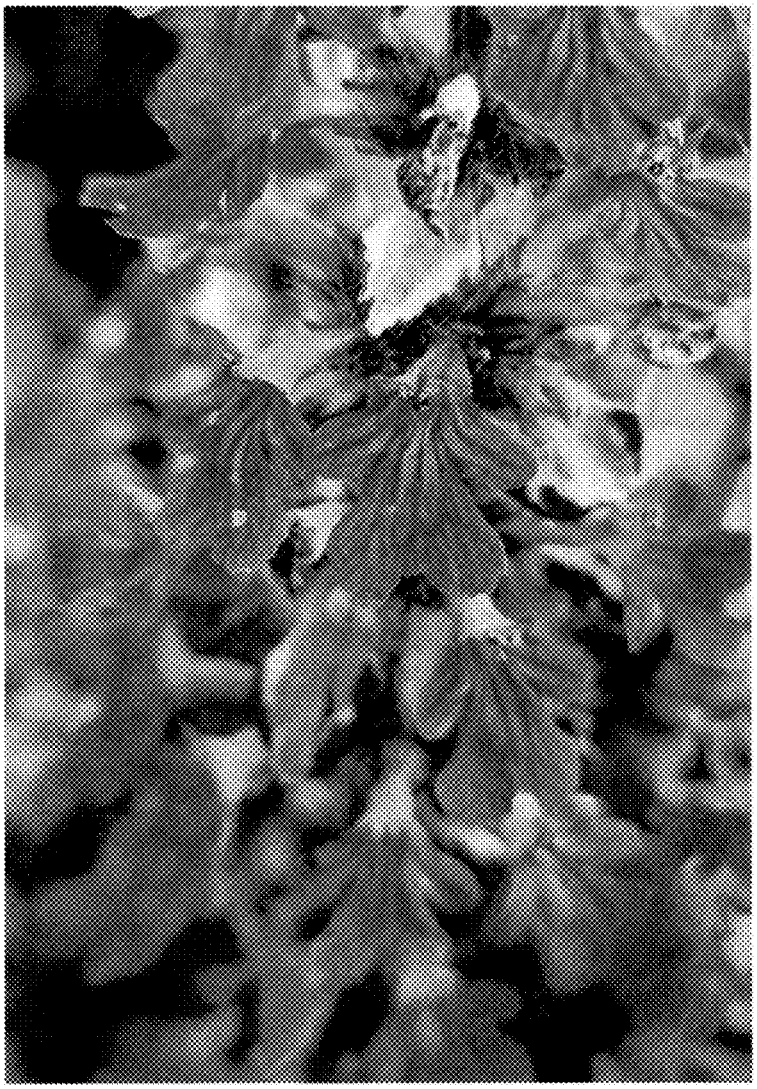
FIG. 2 illustrates a close-up view of the inflorescence.
Figure 3:
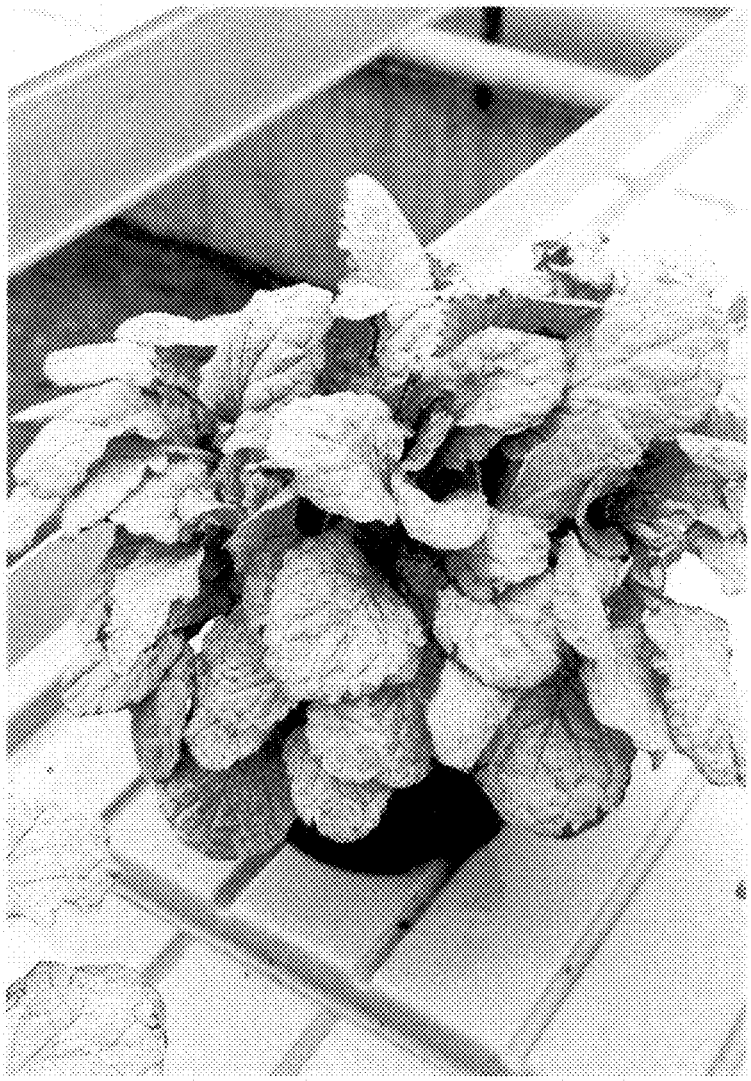
FIG. 3 illustrates a non-flowering plant having typical foliage coloration.

The photographs were taken using conventional techniques and although colors may appear different from actual colors due to light reflectance it is as accurate as possible by conventional photographic techniques.

No artificial light, photoperiodic treatments or chemical treatments were given to the plants.

DETAILED BOTANICAL DESCRIPTION

In the following description, color references are made to The Royal Horticultural Society Colour Chart, 2015 except where general terms of ordinary dictionary significance are used. The following observations and measurements describe 'ASAAJ1' plants grown outdoors in Boskoop, NL. Temperatures ranged from approximately 5° C. to 25° C. during the day and approximately 1° C. to 10° C. at night. No artificial light, photoperiodic treatments or chemical treatments were given to the plants. Measurements and numerical values represent averages of typical plant types. Botanical classification: *Ajuga reptans* 'ASAAJ1'.

PROPAGATION

Type of propagation typically used: Terminal vegetative cuttings.

Time to initiate roots: About 25 days at approximately 20° C.

Root description: Fine, fibrous, brown, not accurately measured with a color chart.

PLANT

Age of plant described: Approximately 1.5 years.

Container size of the plant described: 13 cm.

Plant type: Perennial.

Growth habit: Low, compact, spreading, dense.

Height: 11 cm to top of highest leaf. Approximately 18 cm to top of highest inflorescence.

Plant spread: 45 cm.

Growth rate: Moderately vigorous.

Branching characteristics: Basal.

Length of primary lateral branches: Average range 10 to 15 cm.

Diameter of lateral branches: Average 3 mm.

Quantity of primary lateral branches: Average range 20 to 30.

Characteristics of primary lateral branches:

*Form*.—Quadrangular with obtuse angles.

*Color*.—RHS Purple N77B.

*Texture*.—Glabrous.

*Strength*.—Moderately strong.

*Appearance*.—Glossy.

FOLIAGE

Leaf:

*Arrangement*.—Opposite, single.

*Average length*.—Approximately 5.2 cm.

*Average width*.—Approximately 2.5 cm.

*Shape of blade*.—Spatulate.

*Apex*.—Obtuse.

*Base*.—Narrow cuneate.

*Margin*.—Irregular angulate, strongly undulate.

*Texture of top surface*.—Smooth, sparsely pubescent.

*Texture of bottom surface*.—Smooth, glabrous.

*Color*.—Young foliage upper side: RHS Yellow-Green 144A. Young foliage, under side: RHS Yellow-Green 144B. Mature foliage, upper side: RHS Greyed-Green 191A mixed with 191B, margins Green 139A. Mature foliage, under side: RHS Green N137D.

*Venation*.—Type: Pinnate. Color: Near RHS Greyed-Green 189A.

*Petiole*.—Length: 2.5 cm. Width: 4 mm. Texture: Smooth, glabrous. Strength: Strong. Color: Upper side: RHS Yellow-Green 144A, with Purple N77B towards base. Under side: RHS Yellow-Green 144C and 144D, with Purple N77B towards base.

FLOWER

Natural flowering season: Late spring to late summer.

Inflorescence type: Raceme, individual flowers in clusters of 5 in leaf-axis.

Inflorescence size:

*Height*.—Approximately 6.8 cm.

*Width*.—Approximately 4.3 cm.

*Quantity of flowers per inflorescence*.—Average 80.

Flowers:

*Flower type*.—Labiate, single.

*Length*.—Approximately 0.7 cm.

*Diameter*.—Approximately 0.8 cm.

*Depth*.—Approximately 1.3 cm.

*Throat diameter*.—0.2 cm.

*Tube length*.—0.7 cm.

*Tube diameter*.—0.2 cm.

*Longevity on plant*.—About 10 days.

*Persistent or self-cleaning*.—Self-cleaning.

*Fragrance*.—None.

Petals:

*Arrangement*.—Labiate.

*Quantity per flower*.—Average 5 fused petals (2 very small upper petals, 2 lateral petals and 1 larger lower petal).

*Length*.—Upper petals: 0.1 cm. Lateral petals: 0.3 cm. Lower petal: 0.4 cm.

*Width*.—Upper petals: 0.2 cm. Lateral petals: 0.3 cm. Lower petal: 0.5 cm.

*Margin*.—Entire.

*Shape*.—Upper petals: Short obovate. Lateral petals: Short oblong. Lower petal: Obovate.

*Apex*.—Upper petals: Obtuse. Lateral petals: Obtuse. Lower petal: Cleft into two lobes, tips of lobes obtuse.

*Base*.—Fused.

*Petal texture*.—Upper Surface: Glabrous. Lower Surface: Slightly pubescent.

*Petal color, when opening*.—Upper petals: Upper Surface: RHS Violet-Blue 97B, veins 97A. Lower Surface: RHS Violet-Blue 97B blended with 97C. Lateral petals: Upper Surface: RHS Violet-Blue 97B, veins 95A. Lower Surface: RHS Violet-Blue 97B blended with 97C. Lower petal: Upper Surface: RHS Violet-Blue 92B, veins 95A. Lower Surface: RHS Violet-Blue 97B blended with 97C.

*Petal color, fully opened*.—Upper petals: Upper Surface: RHS Violet-Blue 96C. Lower Surface: RHS Violet-Blue 94D. Lateral petals: Upper Surface: RHS Violet-Blue 96C, veins 95B. Lower Surface: RHS Violet-Blue 94D. Lower petal: Upper Surface: RHS Violet-Blue 96C, veins 95B. Lower Surface: RHS Violet-Blue 94C.

*Tube color*.—RHS Violet-Blue 98C.

Bud:

*Shape*.—Oblanceolate.

*Length*.—Approximately 0.8 cm.

*Diameter*.—Approximately 0.3 cm.

*Color*.—RHS Yellow-Green 144B and 144C.

*Texture*.—Pubescent.

Calyx:

*Shape*.—Rotate, tubular.

*Length*.—0.4 cm.
*Diameter*.—0.3 cm.

Sepals:
*Arrangement*.—Rotate.
*Quantity*.—5 per flower.
*Shape*.—Ovate, lower part fused.
*Tip*.—Acute.
*Base*.—Fused.
*Margin*.—Entire.
*Texture*.—Upper Surface: Glabrous. Lower surface: Pubescent.
*Color*.—RHS Green-White 157A, margins Green 143B.

REPRODUCTIVE ORGANS

Stamens: (Androecium):
*Number*.—4.
*Filament length*.—Approximately 0.4 cm.
*Filament color*.—RHS Violet-Blue 97D.
*Anther size*.—Less than 1 mm in length and width.
*Anther color*.—RHS Black 202A.
*Anther shape*.—Dorsifixed.
*Pollen color*.—RHS Yellow 8C.
*Pollen quantity*.—Moderate.

Pistil: (Gynoecium):
*Number*.—1.
*Length*.—Approximately 0.1 cm.
*Style color*.—RHS Violet-Blue 97B.
*Style length*.—0.9 cm.
*Stigma*.—Shape: Cleft. Color: RHS Blue 108C.
*Ovary color*.—RHS Yellow-Green 144C.

OTHER CHARACTERISTICS

Fruits and seeds: Not observed to date.
Temperature tolerance: Tolerates temperatures from approximately −29° C. to at least 40° C.
Disease/pest resistance: Neither resistance nor susceptibility to normal diseases and pests of *Ajuga* observed.
Drought tolerance: No drought resistance observed.

What is claimed is:

1. A new and distinct cultivar of *Ajuga* plant named 'ASAAJ1' as herein illustrated and described.

* * * * *